United States Patent [19]

Barrett et al.

[11] 3,989,812
[45] Nov. 2, 1976

[54] FOLIC ACID DERIVATIVES AND USE IN RADIO-ASSAY

[75] Inventors: M. James Barrett, Saratoga; Joseph I. De Graw, Sunnyvale, both of Calif.

[73] Assignee: SmithKline Instruments, Inc., Palo Alto, Calif.

[22] Filed: Aug. 9, 1974

[21] Appl. No.: 495,982

[52] U.S. Cl. .............................. 424/1; 260/112.5 R; 23/230 B; 206/84
[51] Int. Cl.$^2$ ................ A61K 43/00; C07C 103/52; A61N 5/12
[58] Field of Search ............... 260/112.5; 424/1, 1.5

[56] References Cited
OTHER PUBLICATIONS

Baugh et al.: Biochim. Biophys. Acta, 212, pp. 116–125 (1970).
Plante et al.: J. Biol. Chem., 242, pp. 1466–1476 (1967).
Boothe et al.: J. Am. Chem. Soc., 70, pp. 1099–1102 (1948).
Boothe et al.: J. Am. Chem. Soc., 71, pp. 2304–2308 (1949).
Cooperman et al.: Chem. Abstr. 67:71459a (1967).
Rothenberg et al.: Chem. Abstr. 74:96929m (1971).
Mitta et al.: Chem. Abstr. 68:69303x (1968).
Radichevich et al.: Chem. Abstr. 67:506c (1967).

*Primary Examiner*—Lewis Gotts
*Assistant Examiner*—Reginald J. Suyat
*Attorney, Agent, or Firm*—Richard D. Foggio; William H. Edgerton

[57] ABSTRACT

Novel folic acid derivatives useful for radio-assaying folic acid and its metabolites in biological liquids are prepared from pteroyl-γ-glutamyl-tyrosines by iodination with $I^{125}$ or $I^{131}$.

4 Claims, No Drawings

FOLIC ACID DERIVATIVES AND USE IN RADIO-ASSAY

This invention relates to novel folic acid derivatives useful for radio-assaying folic acid and its metabolites in biological liquids, such as serum, and to methods of radio-assaying biological liquids using these novel derivatives.

In the past the measurement of folic acid and its derivatives in biological liquids required the use of microorganisms whose growth is dependent only on the presence of folic acid and its derivatives in an incubation medium containing otherwise all other components necessary for growth. This technique is cumbersome, requiring special equipment and facilities not ordinarily available to the usual laboratory.

The use of radio-assays for folic acid and its derivatives while somewhat simpler has required the use of folic acid or its derivatives labelled with radioactive hydrogen (tritium). The measurement of the radioactivity of tritium in addition to requiring a liquid scintillation counter is subject to a variety of errors when unextracted, unpurified biological liquids are used.

It is an object of this invention to provide a novel folic acid derivative which is useful in a radio-assay for folic acid and its metabolites in biological liquids.

It is a further object of this invention to provide a method of radio-assaying for folic acid and its metabolites in biological liquids using a novel folic acid derivative.

It is another object of this invention to provide a method of radio-assaying for folic acid and its metabolites in unextracted biological liquids which includes using a gamma scintillation counter instead of a liquid scintillation counter.

It is an additional object to provide a radio-assay material comprised of a novel folic acid derivative for radio-assaying for folic acid and its metabolites.

The folic acid derivatives of this invention are represented by the following general structural formula:

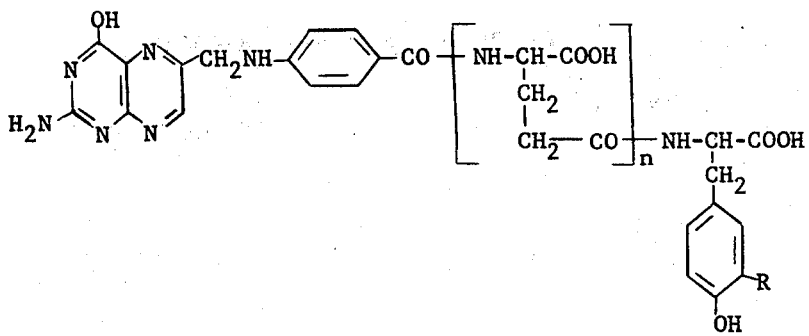

FORMULA I in which:

$n$ is a positive integer of from 1 to 3; and

R is radioactive iodine, such as $I^{125}$ or $I^{131}$.

The compounds of formula I are therefore pteroyl-glutamyl-tyrosines having up to 3 glutamate residues and substituted in the tyrosine moiety with radioactive iodine in the position ortho to the hydroxy group. Preferred compounds of formula I are those wherein n is 1 and R is $I^{125}$.

The compounds of this invention are prepared from a sequence of reactions illustrated by the following preparation of the intermediate pteroyl-γ-glutamyl-tyrosine:

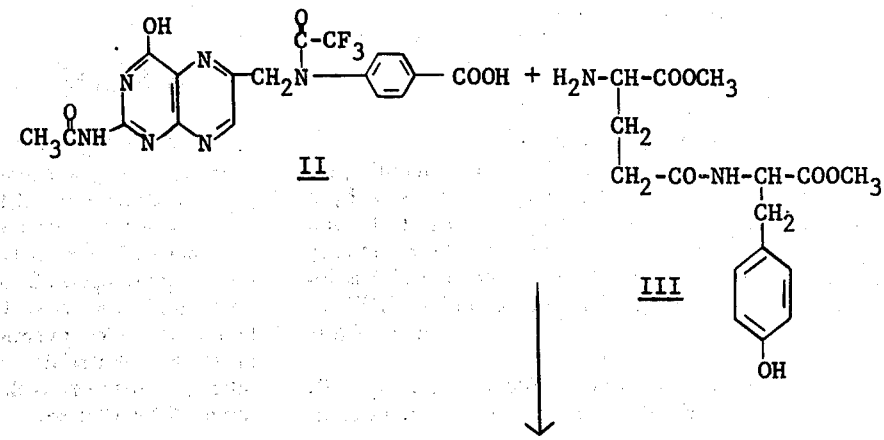

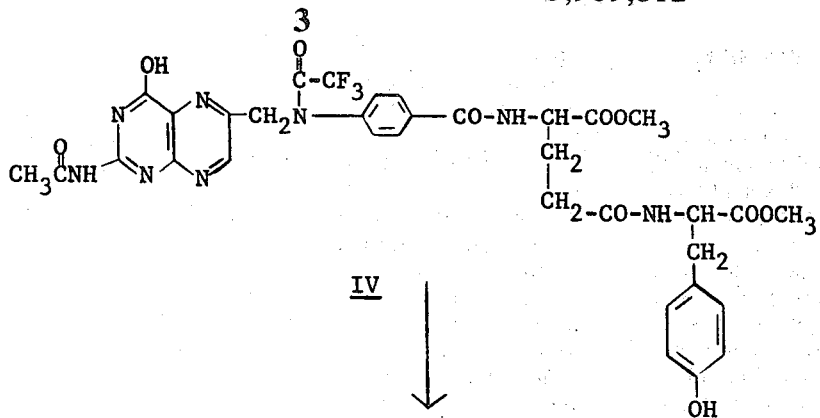

IV

↓

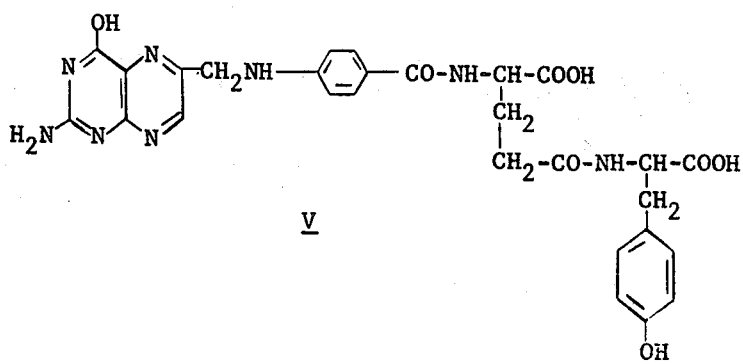

V

Thus, N-protected pteroic acid (II) is first treated with isobutylchloroformate in an unreactive organic solvent such as dimethylformamide or methylene chloride and in the presence of a tertiary amine such as triethylamine or N-methylmorpholine to give the mixed anhydride which is then reacted with the dipeptide diester (III) as shown above to form the N-protected pteroyl tripeptide diester (IV). The latter intermediate is hydrolyzed with an alkali metal hydroxide such as sodium hydroxide to give the free tripeptide (V).

The compounds of formula I are conveniently prepared from a desiodo intermediate such as V by a method based on the work of Greenwood, F. C. and Hunter, W. M. Biochem. J. 89 114 (1963). Exemplary of this method, pteroyl-γ-glutamyl-tyrosine (V) is iodinated with sodium [$I^{125}$] iodide or sodium [$I^{131}$] iodide to give the iodinated tripeptide products of formula I.

Similarly, polyglutamyl peptides corresponding to III employed as described above furnish derivatives comparable to V which are then iodinated to give the products of formula I where n is greater than one. Such polyglutamyl peptides are prepared by well known synthetic routes.

It will be appreciated that the desiodo compounds are useful intermediates for the preparation of the compounds of formula I and as such form a part of the invention. These intermediates are represented by the following formula:

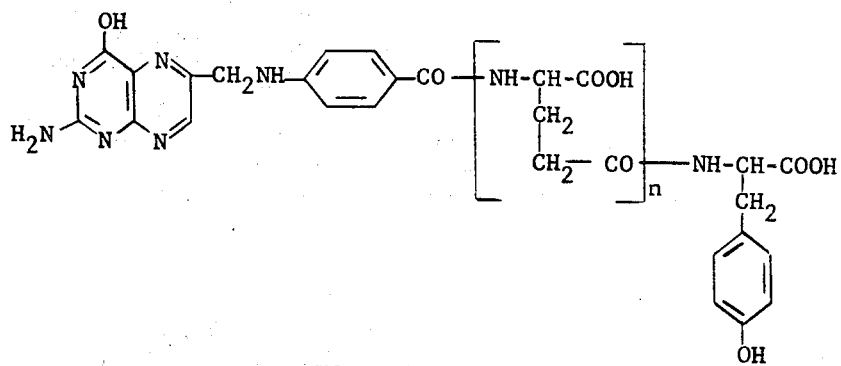

FORMULA VI in which n is a positive integer of from 1 to 3.

The foregoing is a general description of how to prepare the compounds of this invention. However, other methods for the preparation of pteroyl-γ-glutamyl-tyrosines will be obvious to those skilled in the art. The following examples illustrate the preparation of specific compounds and as such should not be construed as limitations of the invention since appropriate variations in starting materials or intermediates will produce other products set forth hereinabove. Also within the scope of this invention are other tyrosine derivatives of a variety of folic acid compounds only differing slightly from pteroylglutamic acid including but not limited to various reduced, substituted and polyglutamyl derivatives.

PREPARATION OF PTEROYL-γ-GLUTAMYL-TYROSINE 1. 2-Acetamido-4-hydroxypteridine-6-aldehyde To a solution of 25.0 g (0.19 mole) of 1,3,3-trimethoxy-1-propene in 75 ml of ether at 5° C is added 22.4 g (0.14 mole) of bromine (bromine color begins to persist at this point) over a period of 40 minutes. The solvent is removed in vacuo at 25° C and the colorless liquid residue is added dropwise with stirring to a mixture of 25 g of sodium bicarbonate and 80 ml of 75% v/v dioxane at 0°–5° C. Stirring is continued for 30 minutes and the mixture is extracted with 200 ml and 150 ml portions of ether. The extract is dried over magnesium sulfate, evaporated in vacuo and the residue distilled through a Vigreux head to afford 2-bromo-3,3-dimethoxypropionaldehyde, b.p. 70°–73° C/8 mm.

To a solution of 24 g (0.286 mole) of sodium bicarbonate in 470 ml of water is slowly added 16.8 g (0.078 mole) of 2,5,6-triamino-4-hydroxypyrimidine dihydrochloride. Then at 20° C is added 14.0 g (0.071 mole) of the above prepared bromoaldehyde over 10 minutes with vigorous stirring. The mixture is stirred for 1 hour, followed by treatment with 16.8 ml of 30% hydrogen peroxide in 360 ml of water. After 1 ½ hours another 8.4 ml of 30% hydrogen peroxide in 180 ml of water is added and the mixture is stirred 15 hours at ambient temperature. The dark blue solid is collected, washed with water and dissolved in 56 ml of 10% sodium hydroxide. Another 13 g of sodium hydroxide is added and the mixture stirred into solution. The solution is chilled 5 hours and the precipitated sodium salt is collected. The material is dissolved in 500 ml of warm water and the pH adjusted to 6–7. The precipitate is collected, washed with water and dried to leave 2-amino-4-hydroxy-6-dimethoxymethylpteridine.

A mixture of 5.2 g of the above acetal, 0.4 ml of pyridine and 80 ml of acetic anhydride is heated at 100°–110° for 6 hours. The mixture is rapidly filtered while hot and the filtrate kept at ambient temperature for 15 hours. The crystalline precipitate is collected, washed with acetic anhydride and dried to yield 2-acetamido-4-hydroxy-6-dimethoxymethylpteridine.

The acetal (4.8 g) is dissolved in 24 ml of 90% formic acid and after 4 hours the precipitated solid is collected, washed with ether and dried to leave the formic acid solvate of 2-acetamido-4-hydroxypteridine-6-aldehyde. This material is suspended in 35 ml of dimethylformamide, warmed to 120° C and cooled to yield the corresponding dimethylformamide solvate.

2. Pteroic Acid

A mixture of 3.07 g (10 mmole) of the dimethylformamide solvate of 2-acetamido-4-hydroxypteridine-6-aldehyde, 3.30 g (20 mmole) of ethyl p-aminobenzoate and 50 ml of glacial acetic acid is stirred at ambient temperature for 30 minutes. To the resulting suspension is added dropwise 1.00 g of dimethylamine borane in 15 ml of acetic acid. The mixture is stirred for an additional 20 minutes, heated to 60° C for 10 minutes and cooled to 25° C. The precipitate is collected by filtration, washed with acetic acid and ether and then dried. The crude product is crystallized from 50 ml of dimethylformamide, with dilution by 20 ml ether, to yield ethyl $N^2$-acetylpteroate.

The ester (2.64 g) is hydrolyzed by heating with 350 ml of 0.1 N sodium hydroxide at 100° C for 30 minutes (under nitrogen and protected from light). The solution is cooled to 20° C and adjusted to pH 3 with concentrated hydrochloric acid. The precipitate is collected by centrifugation at 300 rpm. After washing twice with water and freeze drying, the product pteroic acid is obtained.

Treatment of the pteroic acid (1.80 g) with trifluoroacetic anhydride (40 ml) at reflux for 6 hours, followed by evaporation and digestion of the residue with water yields the 10-trifluoroacetyl acid. A mixture of the latter (2.60 g) and 60 ml of acetic anhydride is stirred at 115° C for 6 hours. The solvent is removed in vacuo and the residue is dissolved in 20 ml of hot dimethylformamide. Hot water (25 ml) is then added and the solution is allowed to stand for 24 hours. The precipitate is collected, similarly recrystallized and finally washed with water and dried to leave $N^2$-acetyl-$N^{10}$-trifluoroacetylpteroic acid (II).

3. γ-Glutamyl-tyrosine Dimethyl Ester

A mixture of 28.1 g of L-N-carbenzoxyglutamic acid, 5.0 g of paraformaldehyde, 1.0 g of p-toluenesulfonic acid and 700 ml of benzene is heated at reflux for 7 hours. The solution is washed with three 200 ml portions of water and extracted with three 250 ml portions of 5% sodium bicarbonate. The combined bicarbonate extract is acidified (ice cooling) to pH 2–3 with 6 N hydrochloric acid and extracted with three 250 ml portions of ethyl acetate. The ethyl acetate is washed with three 200 ml portions of water, dried over magnesium sulfate and evaporated in vacuo to leave N-carbobenzoxy-4-(β-carboxyethyl)-oxazolidin-5-one. The oxazolidinone (20.5 g, 70 mmole) and 7.1 g (70 mmole) of triethylamine are dissolved in 320 ml of dichloromethane and treated with a solution of 9.5 g (70 mmole) of isobutylchloroformate in 320 ml of dichloromethane, dropwise with stirring at −15° C. After 15 minutes a solution of 16.2 g (70 mmole) of L-tyrosine methyl ester hydrochloride and 7.1 g (70 mmole) of triethylamine in 80 ml of dichloromethane is added and the reaction mixture is kept at ambient temperature for 20 hours. The solution is washed with 1 N hydrochloric acid, 5% sodium bicarbonate and water followed by drying over magnesium sulfate. Evaporation of the solvent affords a syrup. This material is dissolved in 400 ml of methanol, diluted with 300 ml of 1 N sodium hydroxide and the solution is kept at room temperature for 5 hours. After acidification with 6 N hydrochloric acid at pH 2, the methanol is removed in vacuo and the aqueous solution extracted three times with 200 ml portions of ethyl acetate. The extract is in turn extracted with three 250 ml portions of 5% sodium bicarbonate. The bicarbonate solution is acidified to pH 2 and extracted with three 200 ml portions of ethyl acetate. The organic extract is washed with water, dried over magnesium sulfate and evaporated in vacuo to leave N-carbobenzoxy-γ-glutamyl-tyrosine.

A solution of the N-carbobenzoxy peptide acid (3.00 g) in 80 ml of 1.5% hydrogen chloride in methanol is kept at ambient temperature for 18 hours. The solvent is evaporated in vacuo at 25° C and the residue is partitioned between 20 ml of water and 25 ml of chloroform. After another 25 ml chloroform extraction, the chloroform is washed with 20 ml of 5% sodium bicarbonate, 20 ml of water and dried over magnesium sulfate. The solvent is removed in vacuo to leave a clear syrup, N-carbobenzoxy-γ-glutamyl-tyrosine dimethyl ester.

A mixture of the N-carbobenzoxy ester prepared above (2.61 g), 260 mg of 10% palladium/carbon, 6.0 ml of 1 N hydrochloric acid and 50 ml of methanol is shaken with hydrogen (3 atmospheres) for 4 hours. The catalyst is removed by filtration and the solvent evaporated in vacuo to leave, as a clear syrup, γ-glutamyl-tyrosine dimethyl ester hydrochloride (III).

4. Pteroyl-γ-glutamyl-tyrosine

To a solution of 1.80 g (4.0 mmole) of the above prepared $N^2$-acetyl-$N^{10}$-trifluoroacetylpteroic acid in 35 ml of dimethylformamide is added 0.61 g (6.0 mmole) of triethylamine followed by 0.55 g (4.0 mmole) of isobutylchloroformate. The mixture is stirred at 25°–30° C for 1 hour, when another 1.00 g (9.9 mmole) of triethylamine and 3.75 g (10.0 mmole) of the above prepared γ-glutamyl-tyrosine dimethyl ester hydrochloride are added. The mixture is stirred for 25 hours at ambient temperature and the solvent evaporated in vacuo. The residue is washed by successively stirring with 75 ml of 0.5 N hydrochloric acid and 80 ml of 5% sodium bicarbonate. The blocked intermediate (IV) is then hydrolyzed with 30 ml of 0.1 N sodium hydroxide at 95°–100° C under nitrogen for 25 minutes. The yellow solution is adjusted to pH 2-3 with 6N hydrochloric acid and the microcrystalline precipitate is collected by centrifugation at 3000 rpm. The material is similarly washed three times with water and the pellet lyophilized to yield pteroyl-γ-glutamyl-tyrosine (V). Chromatography of a 19 mg sample on DEAE-cellulose (8 g absorbent, 1 cm × 35 cm column, UV monitored at 270 nm) with elution by 0.01 M phosphate buffer, pH 7.2, containing 0.2 M sodium chloride shows only one component and affords pure compound after acidification.

IODINATION OF PTEROYL-γ-GLUTAMYL-TYROSINE

To a solution composed of 100 μl of 0.1 N sodium hydroxide containing 1 mCi of $NaI^{125}$, 20 μl 0.5M sodium phosphate, monobasic ($NaH_2PO_4$) and 10 μl 0.5 M sodium phosphate, pH 7.4, is added 10 μg of pteroyl-γ-glutamyl-tyrosine in phosphate buffer (.05 M, pH 7.4) and 20 μl of a 5 mg/ml solution of freshly prepared chloramine T in 0.05 M phosphate buffer pH 7.4. After 15 seconds 20 μl of a 5 mg/ml solution of sodium metabisulfite ($Na_2S_2O_5$) in 0.05 M phosphate buffer pH 7.4 is added. The entire reaction mixture is applied to a 1 × 20 cm column of BioGel-P2 (Bio Rad Laboratories, Richmond, Cal.) and elution is carried out with a buffer consisting of 0.1 M sodium chloride, 0.02 M sodium phosphate pH 7.4 and 0.1% mercaptoethanol. Fractions of volume 0.25 ml are collected and the fractions containing the iodinated pteroyl-γ-glutamyl tyrosine (usually fractions 68 through 104) are collected and pooled. The pooled fractions are applied to a 1 × 20 cm column of DEAE ion-exchange resin initially equilibrated with a solution of 0.01 M sodium chloride, 0.1% mercaptoethanol and 0.02 M phosphate pH 6.7. The applied sample is washed into the column with 6 ml of the equilibration buffer. The column is developed first with 11.5 ml of 0.4 M sodium chloride in 0.02 M sodium phosphate buffer pH 6.7 containing 0.1% mercaptoethanol and then with 80 ml of buffer formed from a linear gradient of sodium chloride from 0.4 M to 1.0 M in 0.02 M sodium phosphate buffer pH 6.7 containing 0.1% mercaptoethanol. Fractions of 3 ml are collected and the fractions containing iodinated pteroyl-γ-glutamyl tyrosine are collected (usually fractions 24 through 34).

ASSAY OF FOLIC ACID DERIVATIVES

There are many methods known for the radio-assay of folic acid and its derivatives in biological fluids. The one described below based on Dunn, R. T., and Foster, L. B., Clinical Chem. 19, 1101 (1973) is meant to be illustrative but other methods obvious to those skilled in the art are also within the scope of this invention.

1. To all assay tubes are added 0.5 ml of a solution containing 1.2 g/200 ml water of lysine hydrochloride pH 10.5.
2. Two-hundred microliters of standards containing 1.25, 2.5, 5.0 and 10.0 and 20 nanograms/ml of $N^5$-methyltetrahydrofolic acid dissolved in 0.01 M potassium phosphate pH 7.4 containing 8.6 g sodium chloride and 10 g bovine serum albumin are added to appropriately labelled assay tubes. All tubes are boiled for 15 minutes and then cooled to room temperature.
3. To each tube is added 0.5 ml of $I^{125}$ labelled pteroyl-γ-glutamyl-tyrosine containing approximately 30,000 counts per minute of radioactivity dissolved in 0.4 M potassium phosphate buffer pH 7.6.
4. To all tubes is added 200 μl of a solution containing 100 μg/ml of β-lactoglobin dissolved in 0.4 M potassium phosphate buffer pH 7.6.
5. After incubation at room temperature for 45 minutes, 0.5 ml of a suspension containing 2.5 mg/ml of dextran and 25 mg/ml of activated charcoal (Norit A) is added to each tube. Following incubation for 5 minutes, all tubes are centrifuged at 2000 rpm for 10 minutes, the supernatent fluid decanted into suitable test tubes and counted for radioactivity on a gamma scintillation spectrometer.
6. Biological samples are treated in the same manner as the standards. The results of a typical assay are summarized in Table 1 which can be plotted to give a standard curve.

TABLE 1

| Concentration of standard (ng/ml) (Initial activity added) | Counts per minute in supernatant (31,200) |
|---|---|
| 0 | 22,263 |
| 0.625 | 20,669 |
| 1.25 | 19,135 |
| 2.50 | 14,390 |
| 5.0 | 11,030 |
| 10.0 | 7,287 |
| 20.0 | 4,382 |

The concentration of folic acid in the biological fluid is determined by comparison of the results obtained with the biological fluid to that obtained from a standard curve.

For convenience, the assay material of this invention is made available in an assay kit. Thus a kit sufficient to prepare 100 assay tubes and sufficient to prepare 5 standard curves will have the following contents:

1. 5 Vials of $N^5$-methyltetrahydrofolic acid standard. This will be provided as a lyophilized preparation to be reconstituted in 1.5 ml water, to yield a solution containing 20 ng/ml $N^5$-methyltetrahydrofolic acid.
2. 1 Vial of lysine buffer. This will be provided as a powder which when dissolved in 55 ml water will yield a solution containing 6 mg/ml lysine pH 10.5.
3. 1 Vial of standard diluent. This will contain granulated bovine serum albumin which when dissolved in 20 ml water yields a 6% bovine serum albumin solution pH 7.4.
4. 5 Vials of β-lactoglobin. This will be provided as a granulated powder such that when dissolved in 10 ml water will yield a solution containing 200 ng/ml β-lactoglobin in 0.4 M potassium phosphate buffer pH 7.6.
5. 1 Vial isotope diluent. This will be provided as a granulated powder such that when dissolved in 55 ml water yields an 0.4 M potassium phosphate solution at pH 7.6.
6. 1 Vial of $I^{125}$-pteroyl-γ-glutamyl-tyrosine. This will be provided as a lyophilized preparation such that when dissolved in 55 ml of isotope diluent will yield a solution containing approximately $3 \times 10^4$ cpm/0.5 ml solution.
7. 1 Vial of dextran powder such that when dissolved in 55 ml water yields a solution containing 2.5 mg/ml dextran.
8. 1 Vial of charcoal powder such that when suspended in 55 ml dextran solution will contain 25 mg/ml charcoal (and 2.5 mg/ml dextran).

After all solutions are prepared of the assay material above (using 1 vial of standard per assay run), the assay is carried out as follows.

1. Preparation of standards. A serial dilution at concentrations of 1.25, 2.5, 5 and 10 ng/ml is prepared by adding 0.6 ml of the standard at 20 ng/ml to 0.6 ml of standard diluent. This yields the 10 ng/ml standard. From this solution (10 ng/ml standard) 0.6 ml is removed and added to 0.6 ml standard diluent to yield a 5 ng/ml standard. This is repeated until 1.25 ng/ml standard is prepared.
2. To properly labelled 13 × 100 cm glass test tubes are added 0.5 ml lysine buffer.
3. To the test tubes labelled reagent blank and 0 standard add 0.2 ml standard diluent. To all other test tubes add 0.2 ml of the appropriate standard or patient serum.
4. Heat tubes in boiling water for 15 minutes and then allow to cool to room temperature.
5. To all tubes add 0.5 ml isotope solution.
6. To all tubes except reagent blank add 100 ml β-lacto globin solution.
7. Incubate 45 minutes at room temperature.
8. Add 0.5 ml of the charcoal dextran suspension. Mix the suspension well before adding. Mix each tube well and incubate 5 minutes at room temperature.
9. Centrifuge for 10 minutes at room temperature at 2,000 rpm.
10. Decant the supernatant into appropriately labelled counting vials and determine the radioactivity using a gamma scintillation spectrometer.
11. Plot the counts per minute observed for each standard versus the concentration of each standard after subtracting the counts per minute observed for the reagent blank from the count rate observed for each standard or patient sample. The value for unknown samples may be determined from the standard curve.

Any folic acid metabolite or derivative which binds to β-lactoglobin can be assayed using the $I^{125}$- or $I^{131}$-pteroyl-γ-glutamyl-tyrosines. Among those known to bind are methotrexate, $N^5$-formyltetrahydrofolic acid, $N^{10}$-methylpteroylglutamic acid, diopterin, pteropterin, $N^5$-methyltetrahydrofolic acid (the standard normally used in the assay) and folic acid itself.

What is claimed is:
1. A chemical compound of the formula:

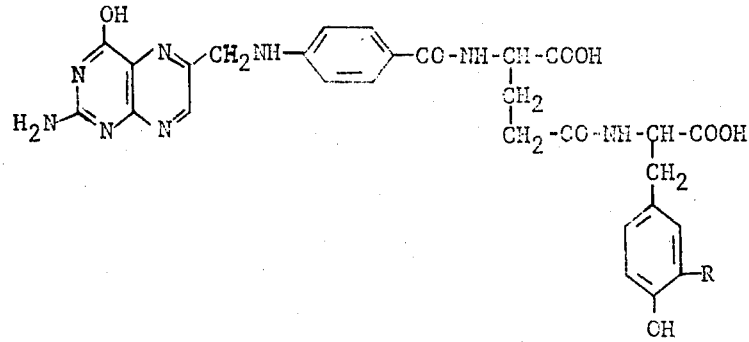

wherein R is radioactive iodine: $I^{125}$ or $I^{131}$.

2. A chemical compound according to claim 1 in which R is $I^{125}$.

3. In a radioassay material for radioassaying a specimen for folic acid, its metabolites or derivatives which bind to β-lactoglobin, the improvement which comprises employing therein a chemical compound of claim 1.

4. The material of claim 3 in which R is $I^{125}$.

* * * * *